US006534489B1

United States Patent
Jomaa

(10) Patent No.: US 6,534,489 B1
(45) Date of Patent: Mar. 18, 2003

(54) ORGANOPHOSPHORUS COMPOUNDS AND THE USE THEREOF

(75) Inventor: Hassan Jomaa, Giessen (DE)

(73) Assignee: Jomaa Pharmaka GmbH, Giessen (DE)

(*) Notice: Subject to any disclaimer, the term of this patent is extended or adjusted under 35 U.S.C. 154(b) by 0 days.

(21) Appl. No.: 09/856,789

(22) PCT Filed: Nov. 20, 1999

(86) PCT No.: PCT/EP99/08966

§ 371 (c)(1),
(2), (4) Date: May 25, 2001

(87) PCT Pub. No.: WO00/31085

PCT Pub. Date: Jun. 2, 2000

(30) Foreign Application Priority Data

Nov. 25, 1998 (DE) .......................................... 198 54 403

(51) Int. Cl.⁷ ............................ C07F 9/38; A61K 31/66; A61P 31/04

(52) U.S. Cl. ...................... 514/114; 558/166; 558/169; 558/175

(58) Field of Search ................................ 558/166, 169, 558/175; 514/114

(56) References Cited

U.S. PATENT DOCUMENTS 4,206,156 A * 6/1980 Kamiya et al. ............. 260/944
4,693,742 A    9/1987 Patterson

FOREIGN PATENT DOCUMENTS

| DE | 27 33 658 | 2/1978 |
|----|-----------|--------|
| EP | 0 009 686 | 4/1980 |
| JP | 61106504 A | 5/1986 |
| WO | WO99/52515 | 10/1999 |

OTHER PUBLICATIONS

Neu et al.(1981) "In Vitro and In Vivo Antibacterial Activity of FR–31564, a Phosphonic Acid Antimicrobial Agent", Antimicrobial Agents and Chemotherapy, vol. 19, No. 6, pp. 1013–1023.
Neu et al. (1982) "Synergy of Fosmidomycin (FR–31564) and Other Antimicrobial Agents", Anti–microbial Agents and Chemotherapy, vol. 22, No. 4, pp. 560–563.
Greenwood (1990) "Fosfomycin Trometamol: Activity in Vitro Against Urinary Tract Pathogens", Infection, vol. 18, No. 2, pp. S60–S64.
Chemical Abstracts No. 186456, vol. 93, No. 19, Nov. 10, 1980, Kamiya et al.
Chemical Abstracts No. 166897, vol. 105, No. 19, Nov. 10, 1986, Yamaji et al.
Glabe et al. (1996) "Novel Functionalized Acylphophonates as Phophonoformate Analogs" J. Org. Chem., vol. 61, No. 20, pp. 7212–7216.

* cited by examiner

Primary Examiner—Cecilia Tsang
Assistant Examiner—Kamal Saeed
(74) Attorney, Agent, or Firm—Collard & Roe, P.C.

(57) ABSTRACT

The invention relates to organophosphorus compounds of general formula (I) wherein A corresponds to general formula (II), wherein one or more of the carbon atoms, selected from the group $C_3$, $C_4$, $C_5$ and their respective substituents can be omitted, and at least one substituent of $B_1$ to $B_{10}$ is a $C_{3-8}$ cycloalkyl ($C_{0-9}$) alkyl group, wherein both the $C_{3-8}$ cycloalkyl group and the $C_{0-9}$ alkyl group can have one or more double bonds and one or two carbon atoms of the cycloalkyl group can be substituted by nitrogen, oxygen or sulfur atoms, and wherein both the cycloalkyl group and the alkyl group can be substituted by hydrogen, halogen amine, oxo groups with branched or unbranched $C_{1-9}$ alkyl groups and $C_{2-9}$ alkenyl groups, wherein the $C_{1-9}$ alkyl groups and $C_{2-9}$ alkenyl groups can be substituted by hydrogen, hydroxy, amine, halogen, and oxo groups. The invention further relates to pharmaceutical preparations containing said compounds and to the use thereof for the therapy and prophylaxis of infectious processes in humans and animals, which processes are induced by bacteria, fungi or parasites. The inventive compounds are also used as fungicidal, bactericidal or herbicidal agents in plants.

14 Claims, No Drawings

ORGANOPHOSPHORUS COMPOUNDS AND THE USE THEREOF

CROSS REFERENCE TO RELATED APPLICATIONS

Applicant claims priority under 35 U.S.C. §119 of German Application No. 198 54 403.0 filed Nov. 25, 1998. Applicant also claims priority under 35 U.S.C. §120 of PCT/EP99/08966 filed Nov. 20, 1999. The international application under PCT article 21(2) was not published in English.

This invention relates to organophosphorus compounds and to the salts, esters and amides thereof and to the use thereof for the therapeutic and prophylactic treatment of infections in humans and animals which are caused by viruses, bacteria, fungi and parasites, to the use thereof as a fungicide, bactericide and herbicide in plants. According to the invention, the organophosphorus compounds comprise phosphinoyl derivatives, phosphinic acid derivatives and phosphonic acid derivatives.

In order to widen the range of options for treating humans and animals and for protecting plants, there is an urgent requirement to provide agents which are not only highly active but, unlike other pharmaceutical preparations or phytosanitary agents, also exhibit reduced side-effects and thus constitute a reduced risk to human health.

DE 27 33 658 A has already disclosed phosphonic acid derivatives of the formula $R_1$—$N(OR_2)$—$A$—$P(O)(OH)_2$, in which $R_1$ denotes hydrogen or acyl, $R_2$ denotes hydrogen, Ar-lower-alkyl or acyl and A is a lower alkylene, lower alkenylene or lower hydroxyalkylene group, preferably formyl, acetyl or trimethylene, together with the esters and pharmaceutical salts thereof. These compounds are used for the therapeutic treatment of infections which are caused by bacteria.

The object of the present invention is accordingly to provide alternative substances which are usable in infections by bacteria and also in infections by-viruses, fungi and parasites in humans and animals and as a fungicide, bactericide and herbicide in plants and which meet the above-stated requirements.

This object is utterly surprisingly achieved by the group of substances defined in claim 1. This group of substances exhibits antiinfective action against viruses, bacteria, fungi, uni- and multicellular parasites.

The organophosphorus compounds according to the invention are of the general formula (I):

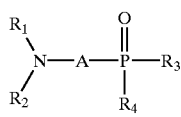
(I)

in which $R_1$ and $R_2$ are identical or different and are selected from the group which consists of hydrogen, substituted and unsubstituted $C_{1-9}$ alkyl, substituted and unsubstituted hydroxy-$C_{1-9}$-alkyl, substituted and unsubstituted $C_{1-9}$ alkenyl, substituted and unsubstituted $C_{1-9}$ alkynyl, substituted and unsubstituted aryl, substituted and unsubstituted acyl, substituted and unsubstituted cycloalkyl, substituted and unsubstituted aralkyl, substituted and unsubstituted heterocyclic residue, halogen, $OX_1$ and $OX_2$, wherein $X_1$ and $X_2$ may be identical or different and are selected from the group which consists of hydrogen, substituted and unsubstituted $C_{1-9}$ alkyl, substituted and unsubstituted hydroxy-$C_{1-9}$-alkyl, substituted and unsubstituted $C_{1-9}$ alkenyl, substituted and unsubstituted $C_{1-9}$ alkynyl, substituted and unsubstituted aryl, substituted and unsubstituted acyl, substituted and unsubstituted cycloalkyl, substituted and unsubstituted aralkyl, substituted and unsubstituted heterocyclic residue, in which A is of the following formula (II):

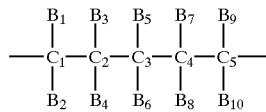

wherein one or more of the carbon atoms selected from the group $C_3$, $C_4$, $C_5$ together with their substituents may also be absent, and at least one substituent present in the range from $B_1$ to $B_{10}$ is a $C_{3-8}$-cycloalkyl-($C_{0-9}$)-alkyl group, wherein both the $C_{3-8}$ cycloalkyl group and the $C_{0-9}$ alkyl group may comprise one or more double bonds and one or two carbon atoms of the cycloalkyl group may be replaced by nitrogen, oxygen or sulfur atoms, and wherein both the cycloalkyl group and the alkyl group may be substituted with hydroxy, halogen, amino, oxo groups with branched or unbranched $C_{1-9}$ alkyl groups and $C_{2-9}$ alkenyl groups, wherein the $C_{1-9}$ alkyl group and $C_{2-9}$ alkenyl groups may be substituted with hydrogen, hydroxy, amino, halogen and oxo groups, and the remaining substituents $B_1$ to $B_{10}$ present are selected from the group which consists of hydrogen, hydroxy, halogen, amino groups, $C_{1-26}$ alkyl residues, $C_{1-26}$ alkoxy residues, $C_{1-26}$-alkoxy-$C_{1-26}$-alkyl residues or both substituents of a C atom together form an oxo group, wherein each $C_{1-26}$ alkyl residue and each $C_{1-26}$ alkoxy residue may be branched or unbranched and be saturated or unsaturated with one or more double bonds and may be substituted with hydroxy, amino, halogen and oxo groups, in which $R_3$ and $R_4$ are identical or different and are selected from the group which consists of substituted and unsubstituted $C_{1-26}$ alkyl, substituted and unsubstituted hydroxy-$C_{1-26}$-alkyl, substituted and unsubstituted aryl, substituted and unsubstituted acyl, substituted and unsubstituted cycloalkyl, substituted and unsubstituted aralkyl, substituted and unsubstituted $C_{1-26}$ alkenyl, substituted and unsubstituted $C_{1-26}$ alkynyl, substituted and unsubstituted cycloalkyl, substituted and unsubstituted heterocyclic residue, halogen, $OX_3$ and $OX_4$, wherein $X_3$ and X4 are identical or different and are selected from the group which consists of hydrogen, substituted and unsubstituted $C_{1-26}$ alkyl, substituted and unsubstituted hydroxy-$C_{1-26}$-alkyl, substituted and unsubstituted aryl, substituted and unsubstituted aralkyl, substituted and unsubstituted $C_{1-26}$ alkenyl, substituted and unsubstituted $C_{1-26}$ alkynyl, substituted and unsubstituted cycloalkyl, substituted and unsubstituted heterocyclic residue, a silyl, a cation of an organic and inorganic base, in particular a metal of main groups I, II or III of the periodic system, ammonium, substituted ammonium and ammonium compounds derived from ethylenediamine or amino acids, and the pharmaceutically acceptable salts, esters and amides thereof and salts of the esters.

In particular, compounds of the following formula (III) are suitable:

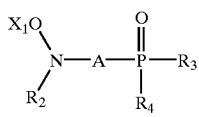

(III)

wherein $X_1$ is preferably a hydrogen and $R_2$ an acyl residue, particularly preferably a formyl residue or acetyl residue.

$X_3$ and $X_4$ $OX_3$ and $OX_4$, and $X_3$ and $X_4$ are preferably hydrogen, a metal of main groups I, II or III of the periodic system, ammonium, substituted ammonium or ammonium compounds derived from ethylenediamine or amino acids. In other words, the salt compounds of the organophosphorus compounds are formed with organic or inorganic bases (for example sodium salt, potassium salt, calcium salt, aluminium salt, ammonium salt, magnesium salt, triethylamine salt, ethanolamine salt, dicyclohexylamine salt, ethylenediamine salt, N,N'-dibenzylethylenediamine salts) as well as salts with amino acids (for example arginine salt, aspartic acid salt, glutamic acid salt etc.) and the like.

The carbon chain of A with the formula (II) preferably consists of three carbon atoms $C_1$, $C_2$, $C_3$.

Further preferred compounds are those in which the carbon chain of A with the formula (II) consists of four carbon atoms $C_1$, $C_2$, $C_3$, $C_4$ and $B_7$ and $B_8$ or both are a hydroxy group. In this case, methylene groups are also preferred for $R_3$ and $R_4$.

It is furthermore preferred that $B_1$ and $B_2$ together form an oxo group. In this case, the carbon chain in A consists of four carbon atoms $C_1$, $C_2$, $C_3$, $C_4$.

It is furthermore preferred that $B_7$ and $B_8$ together form an oxo group. In this case, the carbon chain in A likewise consists of four carbon atoms $C_1$, $C_2$, $C_3$, $C_4$.

The carbon chain preferably consists of the 5 carbon atoms $C_1$, $C_2$, $C_3$, $C_4$, $C_5$, wherein $B_1$ and $B_2$ together form an oxo group and at least one substituent of $B_9$ or $B_{10}$ is a hydroxyl group or $B_9$ and $B_{10}$ together also form an oxo group.

Special features of the above definitions and suitable examples thereof are given below:

"Acyl" is a substituent which originates from an acid, such as from an organic carboxylic acid, carbonic acid, carbamic acid or the thio acid or imidic acid corresponding to the above individual acids, or from an organic sulfonic acid, wherein these acids in each case comprise aliphatic, aromatic and/or heterocyclic groups in the molecule together with carbamoyl or carbamimidoyl.

Suitable examples of these acyl groups are given below.

Aliphatic acyl groups are defined as acyl residues originating from an aliphatic acid and include the following:

alkanoyl (for example formyl, acetyl, propionyl, butyryl, isobutyryl, valeryl, isovaleryl, pivaloyl etc.); alkenoyl (for example acryloyl, methacryloyl, crotonoyl etc.); alkylthioalkanoyl (for example methylthioacetyl, ethylthioacetyl etc.) alkanesulfonyl (for example mesyl, ethanesulfonyl, propanesulfonyl etc.); alkoxycarbonyl (for example methoxycarbonyl, ethoxycarbonyl, propoxycarbonyl, isopropoxycarbonyl, butoxycarbonyl, isobutoxycarbonyl etc.); alkylcarbamoyl (for example methylcarbamoyl etc.); (N-alkyl)thiocarbamoyl (for example (N-methyl) thiocarbamoyl etc.); alkylcarbamimidoyl (for example methylcarbamimidoyl etc.); oxalo; alkoxalyl (for example methoxalyl, ethoxalyl, propoxalyl etc.).

In the above examples of aliphatic acyl groups, the aliphatic hydrocarbon moiety, in particular the alkyl group or alkane residue, may optionally have one or more suitable substituents, such as amino, halogen (for example fluorine, chlorine, bromine etc.), hydroxy, hydroxyimino, carboxy, alkoxy (for example methoxy, ethoxy, propoxy etc.), alkoxycarbonyl, acylamino (for example benzyloxycarbonylamino etc.), acyloxy (for example acetoxy, benzoyloxy etc.) and the like; preferred aliphatic acyl residues with such substituents which may be mentioned are, for example, alkanoyls substituted with amino, carboxy, amino and carboxy, halogen, acylamino or the like.

Aromatic acyl residues are defined as those acyl residues which originate from an acid with a substituted or unsubstituted aryl group, wherein the aryl group may comprise phenyl, toluyl, xylyl, naphthyl and the like; suitable examples are stated below:

aroyl (for example benzoyl, toluoyl, xyloyl, naphthoyl, phthaloyl etc.); aralkanoyl (for example phenylacetyl etc.); aralkenoyl (for example cinnamoyl etc.); aryloxyalkanoyl (for example phenoxyacetyl etc.); arylthioalkanoyl (for example phenylthioacetyl etc.); arylaminoalkanoyl (for example N-phenylglycyl, etc.); arenesulfonyl (for example benzenesulfonyl, tosyl or toluenesulfonyl, naphthalenesulfonyl etc.); aryloxycarbonyl (for example phenoxycarbonyl, naphthyloxycarbonyl etc.); aralkoxycarbonyl (for example benzyloxycarbonyl etc.); arylcarbamoyl (for example phenylcarbamoyl, naphthylcarbamoyl etc.); arylglyoxyloyl (for example phenylglyoxyloyl etc.).

In the above-stated Examples of aromatic acyl residues, the aromatic hydrocarbon moiety (in particular the aryl residue) and/or the aliphatic hydrocarbon moiety (in particular the alkane residue) may optionally have one or more suitable substituents, such as those which have already been stated as suitable substituents for the alkyl group or the alkane residue. Examples of preferred aromatic acyl residues with specific substituents which may in particular be mentioned are aroyl substituted with halogen and hydroxy or with halogen and aralkanoyl substituted with hydroxy, hydroxyimino, dihaloalkanoyloxyimino, together with arylthiocarbamoyl (for example phenylthiocarbamoyl etc.); arylcarbamimidoyl (for example phenylcarbarnimidoyl etc.).

A heterocyclic acyl residue is taken to mean an acyl residue which originates from an acid with a heterocyclic group; such residues include:

heterocyclic carbonyl, in which the heterocyclic residue is an aromatic or aliphatic 5- to 6-membered heterocycle with at least one heteroatom from the group nitrogen, oxygen and sulfur (for example thiophenyl, furoyl, pyrrolecarbonyl, nicotinyl etc.);

heterocycle-alkanoyl, in which the heterocyclic residue is 5- to 6-membered and comprises at least one heteroatom from the group nitrogen, oxygen and sulfur (for example thiophenylacetyl, furylacetyl, imidazolylpropionyl, tetrazolylacetyl, 2-(2-amino4-tiazolyl)-2-methoxyiminoacetyl etc.) and the like.

In the above Examples of heterocyclic acyl residues, the heterocycle and/or the aliphatic hydrocarbon moiety may optionally comprise one or more suitable substituents, such as the same as were stated to be suitable for alkyl and alkane groups.

"Alkyl" is a linear or branched alkyl residue, such as methyl, ethyl, propyl, isopropyl, butyl, isobutyl, tert.-butyl, pentyl, hexyl and the like.

"Hydroxyalkyl" is a linear or branched alkyl residue which comprises at least one hydroxyl group, preferably one or two hydroxyl groups.

"Alkenyl" includes linear or branched alkenyl groups, such as for example vinyl, propenyl (for example 1-propenyl, 2-propenyl), 1-methylpropenyl, 2-methylpropenyl, butenyl, 2-ethylpropenyl, pentenyl, hexenyl.

"Alkynyl" includes linear or branched alkynyl groups.

Cycloalkyl preferably denotes an optionally substituted $C_{3-8}$ cycloalkyl; possible substituents are inter alia alkyl, alkenyl, alkynyl, alkoxy (for example methoxy, ethoxy etc.), halogen (for example fluorine, chlorine, bromine etc.), nitro and the like.

Aryl is an aromatic hydrocarbon residue, such as phenyl, naphthyl etc., which may optionally comprise one or more suitable substituents, such as alkyl, alkenyl, alkynyl, alkoxy (for example methoxy, ethoxy etc.), halogen (for example fluorine, chlorine, bromine etc.), nitro and the like.

"Aralkyl" includes mono-, di-, triphenylalkyls such as benzoyl, phenethyl, benzhydryl, trityl and the like, wherein the aromatic moiety may optionally comprise one or more suitable substituents, such as alkoxy (for example methoxy, ethoxy etc.), halogen (for example. fluorine, chlorine, bromine etc.), nitro and the like.

The residues $X_3$ and $X_4$ may preferably be selected such that esters are formed on the phosphino group or phosphono group. Suitable examples of esters of the formulae (I) and (III) include suitable mono- and diesters, and preferred examples of such esters are alkyl esters (for example hexadecanyl ester, octadecanyl ester etc.); aralkyl esters (benzyl ester, phenethyl ester, benzhydryl ester, trityl ester etc.); aryl esters (for example phenyl ester, tolyl ester, naphthyl ester etc.); aroylalkyl esters (for example phenacyl ester etc.); and silyl esters (for example of trialkylhalosilyl, dialkyldihalosilyl, alkyltrihalosilyl, dialkylarylhalosilyl, trialkoxyhalosilyl, dialkylaralkylhalosilyl, dialkoxydihalosilyl, trialkoxyhalosilyl etc.) and the like.

In the above esters, the alkane and/or arene moiety may optionally comprise at least one suitable substituent, such as halogen, alkoxy, hydroxy, nitro or the like.

The compounds according to the invention according to the formulae (I) and (III) may be present in the protonated form thereof as an ammonium salt of organic or inorganic acids, such as hydrochloric acid, hydrobromic acid, sulfuric acid, nitric acid, methanesulfonic acid, p-toluenesulfonic acid, acetic acid, lactic acid, maleic acid, fumaric acid, oxalic acid, tartaric acid, benzoic acid etc.

The compounds according to the invention of the formulae (I) and (III) permit, for example for groups $R_1$, $R_2$, $R_3$, $R_4$, $X_1$, $X_2$, $X_4$ or A which contain double bonds or are chiral, the occurrence of steric isomers. The use according to the invention of the compounds includes all steric isomers, both as pure substances and in the form of mixtures.

The organophosphorus compounds are in particular suitable for the therapeutic and prophylactic treatment of infections in humans and animals caused by viruses, bacteria, uni- and multicellular parasites and fungi.

The compounds are active against unicellular parasites (protozoa), in particular against the causative organisms of malaria and sleeping sickness and of Chagas' disease, toxoplasmosis, amoebic dysentery, leishmaniases, trichomoniasis, pneumocystosis, balantidiasis, cryptosporidiosis, sarcocytosis, acanthamoebosis, naeglerosis, coccidiosis, giardiasis and lambliasis.

They are accordingly in particular suitable for the prophylactic treatment of malaria and of sleeping sickness and of Chagas' disease, of toxoplasmosis, amoebic dysentery, leishmaniases, trichomoniasis, pneumocystosis, balantidiasis, cryptosporidiosis, sarcocytosis, acanthamoebosis, naeglerosis, coccidiosis, giardiasis and lambliasis.

The active substances according to the invention may in particular be used against the following bacteria:

bacteria of the family Propionibacteriaceae, in particular of the genus Propionibacterium, in particular the species Propionibacterium acnes, bacteria of the family Actinomycetaceae, in particular of the genus Actinomyces, bacteria of the genus Cornynebacterium, in particular the species *Corynebacterium diphtheriae* and *Corynebacterium pseudotuberculosis*, bacteria of the family Mycobacteriaceae, of the genus Mycobacterium, in particular the species *Mycobacterium leprae, Mycobacterium tuberculosis, Mycobacterium bovis* and *Mycobacterium avium,* bacteria of the family Chlamydiaceae, in particular the species *Chlamydia trachomatis* and *Chlamydia psittaci,* bacteria of the genus Listeria, in particular the species *Listeria monocytogenes,* bacteria of the species *Erysipelthrix rhusiopathiae,* bacteria of the genus Clostridium, bacteria of the genus Yersinia, the species *Yersinia pestis, Yersinia pseudotuberculosis, Yersinia enterocolitica* and *Yersinia ruckeri,* bacteria of the family Mycoplasmataceae, of the genera Mycoplasma and Ureaplasma, in particular the species *Mycoplasma pneumoniae,* bacteria of the genus Brucella, bacteria of the genus Bordetella, bacteria of the family Neisseriaceae, in particular of the genera Neisseria and Moraxella, in particular the species *Neisseria meningitides, Neisseria gonorrhoeae* and *Moraxella bovis,* bacteria of the family Vibrionaceac, in particular of the genera Vibrio, Aeromonas, Plesiomonas and Photobacterium, in particular the species *Vibrio cholerae, Vibrio anguillarum* and *Aeromonas salmonicidas,* bacteria of the genus Campylobacter, in particular the species Campylobacterjejuni, Campylobacter coli and *Campylobacter fetus,* bacteria of the genus Helicobacter, in particular the species *Helicobacter pylori,* bacteria of the families Spirochaetaceae and Leptospiraceae, in particular of the genera Treponema, Borrelia and Leptospira, in particular *Borrelia burgdorferi,* bacteria of the genus Actinobacillus, bacteria of the family Legionellaceae, of the genus Legionella, bacteria of the family Rickettsiaceae and family Bartonellaceae, bacteria of the genera Nocardia and Rhodococcus, bacteria of the genus Dermatophilus, bacteria of the family Pseudomonadaceae, in particular of the genera Pseudomonas and Xanthomonas, bacteria of the family Enterobacteriaceae, in particular of the genera Escherichia, Klebsiella, Proteus, Providencia, Salmonella, Serratia and Shigella, bacteria of the family Pasteurellaceae, in particular of the genus Haemophilus, bacteria of the family Micrococcaceae, in particular of the genera Micrococcus and Staphylococcus, bacteria of the family Streptococcaceae, in particular of the genera Streptococcus and Enterococcus and bacteria of the family Bacillaceae, in particular of the genera Bacillus and Clostridium.

Organophosphorus compounds and the derivatives thereof are consequently suitable for treating diphtheria, acne vulgaris, listerioses, swine erysipelas in animals, gas gangrene in humans and animals, malignant oedema in humans and animals, tuberculosis in humans and animals, leprosy and further mycobacterioses in humans and animals, paratuberculosis in animals, plague, mesenterial lymphadenitis and pseudotuberculosis in humans and animals, cholera, legionnaires' disease, borreliosis in humans and animals, leptospiroses in humans and animals, syphilis, Campylobacter enteritis infections in humans and animals, *Moraxella keratoconjunctivitis* and serositis in animals, brucellosis of animals and humans, anthrax in humans and animals, actinomycosis in humans and animals, streptotrichoses, psittacosis/ortnithosis in animals, Q fever, ehrlichiosis.

Use is furthermore effective in the eradication of Helicobacter in ulcers of the gastrointestinal tract.

Combinations with another antibiotic may also be used to treat the above-stated diseases. Isoniazid, rifampicin, ethambutol, pyrazinamide, streptomycin, protionamide and dapsone are in particular suitable for combination preparations with other antiinfective agents for the treatment of tuberculosis.

The active substances according to the invention are furthermore in particular usable in infections with the following viruses:

Parvoviridae: parvoviruses, dependoviruses, densoviruses, Adenoviridae: adenoviruses, mastadenoviruses, aviadenoviruses, Papovaviridae: papovaviruses, in particular papillomaviruses ("wart" viruses), polyomaviruses, in particular JC virus, BK virus and miopapovaviruses, Herpesviridae: all herpesviruses, in particular herpes simplex viruses, varicella-zoster viruses, human cytomegalovirus, Epstein-Barr viruses, all human herpesviruses, human herpesvirus 6, human herpesvirus 7, human herpesvirus 8, Poxiviridae: poxviruses, orthopoxviruses, parapoxviruses, molluscum contagiosum virus, aviviruses, capriviruses, leporipoxviruses, all primarily hepatotropic viruses, hepatitisviruses: hepatitis A viruses, hepatitis B viruses, hepatitis C viruses, hepatitis D viruses, hepatitis E viruses, hepatitis F viruses, hepatitis G viruses, hepadnaviruses: all hepatitisviruses, hepatitis B virus, hepatitis D viruses, Picomaviridae: picomaviruses, all enteroviruses, all polioviruses, all coxsackie-viruses, all echoviruses, all rhinoviruses, hepatitis A virus, aphthoviruses, Calciviridae: hepatitis E viruses, Reoviridae: reoviruses, orbiviruses, rotaviruses, Togaviridae: togaviruses, alphaviruses, rubiviruses, pestiviruses, rubellavirus, Flaviviridae: flaviviruses, FSME virus, hepatitis C virus, Orthomyxoviridae: all influenza viruses, Paramyxoviridae: paramyxoviruses, morbillivirus, pneumovirus, measles virus, mumps virus, Rhabdoviridae: rhabdoviruses, rabies virus, lyssavirus, vascular stomatitisvirus, Coronaviridae: coronaviruses, Bunyaviridae: bunyaviruses, nairovirus, phlebovirus, uukuvirus, hantavirus, hantaan virus, Arenaviridae: arenaviruses, lymphocytic choriomeningitis virus, Retroviridae: retroviruses, all HTL viruses, human T-cell leukaemia virus, oncornaviruses, spumaviruses, lentiviruses, all HI viruses, Filoviridae: Marburg and Ebola virus, slow-virus infections, prions, oncoviruses and leukaernia viruses.

The organophosphorus compounds used according to the invention are consequently suitable for combating the following viral infections:

eradication of papillomaviruses to prevent tumours, in particular tumours of the reproductive organs caused by papillomaviruses in humans, eradication of JC viruses and BK viruses, eradication of herpesviruses, eradication of human herpesvirus 8 to treat Kaposi's sarcoma, eradication of cytomegaloviruses before transplantations, eradication of Epstein-Barr viruses before transplantation and to prevent tumours associated with Epstein-Barr viruses, eradication of hepatitis viruses to treat chronic liver disease and to prevent liver tumours and cirrhosis of the liver, eradication of coxsackie-viruses in cardiomyopathy, eradication of coxsackie-viruses in diabetes mellitus patients, eradication of immunodeficiency viruses in humans and animals, treatment of accompanying infections in AIDS patients, treatment of respiratory tract inflammation of viral causation (laryngeal papilloma, hyperplasia, rhinitis, pharyngitis, bronchitis, pneumonia), of the sensory organs (keratoconjunctivitis), of the nervous system (poliomyelitis, meningoencephalitis, encephalitis, subacute sclerosing panencephalitis, SSPE, progressive multifocal leukoencephalopathy, lymphocytic choriomeningitis), of the gastrointestinal tract (stomatitis, gingivostomatitis, oesophagitis, gastritis, gastroenteritis, diarrhoea), of the liver and gall system (hepatitis, cholangitis, hepatocellular carcinoma), of the lymphatic tissue (mononucleosis, lymphadenitis), of the haemopoietic system, of the reproductive organs (mumps orchitis), of the skin (warts, dermatitis, herpes labialis, herpes febrilis, herpes zoster, shingles), of the mucous membranes (papillomas, conjunctival papillomas, hyperplasia, dysplasia), of the cardiovascular system (arteriitis, myocarditis, endocarditis, pericarditis), of the kidney/urinary system, of the reproductive organs (anogenital lesions, warts, genital warts, sharp condylomas, dysplasia, papillomas, cervical dysplasia, condyloma acuminatum, epidermodysplasia verruciformis), of the locomotory organs (myositis, myalgia), treatment of foot-and-mouth disease in cloven-hoofed animals, of Colorado tick fever, Dengue syndrome, of haemorrhagic fever, of early summer meningoencephalitis (FSME) and of yellow fever.

The described compounds, i.e. the organophosphorus compounds of the formulae (I) and (III) and esters and amides thereof on the phosphino group and salts thereof exhibit strong cytotoxic activity against uni- and multicellular parasites, in particular against the causative organisms of malaria and sleeping sickness. The compounds according to the invention are accordingly usable for the treatment of infective diseases which are caused in humans and animals by viruses, bacteria, parasites and fungi. The compounds are also suitable for the prevention of diseases which are caused by viruses, bacteria, parasites and fungi, in particular for the prophylactic treatment of malaria and of sleeping sickness.

The organophosphorus compounds used according to the invention, which generally include for this purpose pharmaceutically acceptable salts, amides, esters, a salt of such an ester or also compounds which, on administration, provide the compounds used according to the invention as metabolites or breakdown products (also known as "prodrugs"), may be formulated for administration in any suitable manner analogous to known agents having an antiinfective action (mixed with a non-toxic, pharmaceutically acceptable excipient).

Pharmaceutically acceptable salts of the compounds include salts which the compounds of the formulae (I) and (III) according to the invention form in their protonated form as an arnmonium salt of inorganic or organic acids, such as hydrochloric acid, sulfuric acid, citric acid, maleic acid, fumaric acid, tartaric acid, p-toluenesulfonic acid.

Particularly pharmaceutically suitable salts are also those formed by suitable selection of $X_3$ and $X_4$, such as sodium salt, potassium salt, calcium salt, ammonium salt, ethanolamine salt, triethylamine salt, dicyclohexylamine salt and salts of an amino acid such as arginine salt, aspartic acid salt, glutamic acid salt.

The activity of the substances is determined using a test system. This system is based upon in vitro measurement of the inhibition of growth of bacteria, parasites, viruses, fungi or plants. Test methods known to the person skilled in the art are in part used for this purpose.

For example, antimalarial activity is determined by measuring the inhibition of the growth of malaria parasites in blood cultures.

Antibacterial activity is determined on the basis of measuring the inhibition of bacterial growth on nutrient media and in liquid cultures.

Antiviral activity is determined on the basis of the formation of viral elements in cell cultures.

Fungicidal activity is determined on the basis of inhibition of fungal growth on nutrient media and in liquid cultures.

Some of the microorganisms which are to be investigated may only be investigated in animal models. In this case, the appropriate models will then be used.

Substances which exhibit activity in in vitro measurement systems are then further investigated in in vivo models. Antiparasitic, antiviral, fungicidal or antibacterial activity is further evaluated in the appropriate animal models.

Screening for herbicidal activity is determined by means of algal systems and measurement of isoprene emissions from plants under standard conditions.

The pharmaceutically active agents may be prepared in dosage units in the form of pharmaceutical preparations. This means that the preparation is in the form of individual components, for example tablets, coated tablets, capsules, pills, suppositories and ampoules, the active substance content of which corresponds to a fraction or multiple of an individual dose. The dosage units may contain, for example 1, 2, 3 or 4 individual doses or ½, ⅓ or ¼ of an individual dose. An individual dose preferably contains the quantity of active substance which is administered at one time and usually corresponds to a whole, half, third or quarter of a daily dose.

Non-toxic, inert, pharmaceutically suitable excipients should be taken to mean solid, semi-solid or liquid diluents, fillers and formulation auxiliaries of all kinds.

Preferred pharmaceutical preparations which may be mentioned are tablets, coated tablets, capsules, pills, granules, suppositories, solutions, suspensions and emulsions, pastes, ointments, gels, creams, lotions, powders and sprays. Tablets, coated tablets, capsules, pills and granules may contains the active substances together with conventional excipients, such as (a) fillers and extenders, for example starches, lactose, cane sugar, glucose, mannitol and silica, (b) binders, for example carboxymethylcellulose, alginates, gelatine, polyvinylpyrrolidone, (c) humectants, for example glycerol, (d) suspending agents, for example agar-agar, calcium carbonate and sodium carbonate, (e) dissolution retardants, for example paraffin and (f) resorption accelerators, for example quaternary ammonium compounds, (g) wetting agents, for example cetyl alcohol, glycerol monostearate, (h) adsorbents, for example kaolin and bentonite and (i) lubricants, for example talcum, calcium and magnesium stearate and solid polyethylene glycols or mixtures of the substances stated in (a) to (i).

The tablets, coated tablets, capsules, pills and granules may be provided with conventional coatings and shells optionally containing opacifying agents and may also be composed such that they release the active substances only with a delay or preferably in a particular part of the intestinal tract, wherein polymeric substances and waxes may, for example, be used as the matrices.

The active substance or substances, optionally together with one or more of the above-stated excipients, may also be present in microencapsulated form.

In addition to the active substance or substances, suppositories may contain conventional water-soluble or water-insoluble excipients, for example polyethylene glycols, fats, for example cocoa butter and higher esters (for example $C_{14}$ alcohol with $C_{16}$ fatty acid) or mixtures of these substances.

In addition to the active substance or substances, ointments, pastes, creams and gels may contain conventional excipients, for example animal and vegetable fats, waxes, paraffins, starch, gum tragacanth, cellulose derivatives, polyethylene glycols, silicones, bentonites, silica, talcum and zinc oxide or mixtures of these substances.

In addition to the active substance or substances, powders and sprays may contain conventional excipients, for example lactose, talcum, silica, aluminium hydroxide, calcium silicate and polyamide powder or mixtures of these substances. Sprays may additionally contain conventional propellants, for example chlorofluorocarbons.

In addition to the active substance or substances, solutions and emulsions may contain conventional excipients, such as solvents, solubilising agents and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cottonseed oil, peanut oil, corn oil, olive oil, castor oil and sesame oil, glycerol, glycerol formal, tetrahydrofurfuryl alcohol, polyethylene glycols and sorbitan fatty acid esters or mixtures of these substances.

For parenteral administration, the solutions and emulsions may also be present in sterile, isotonic form.

In addition to the active substance or substances, suspensions may contain conventional excipients, such as liquid diluents, for example water, ethyl alcohol, propylene glycol, suspending agents, for example ethoxylated isostearyl alcohols, polyoxyethylene sorbitol and sorbitan esters, microcrystalline cellulose, aluminium metahydroxide, bentonite, agar-agar and gum tragacanth or mixtures of these substances.

The stated formulations may also contain colorants, preservatives and odour- or flavour-enhancing additives, for example peppermint oil and eucalyptus oil, and sweeteners, for example saccharin.

The active substances of the formulae (I) and (III) should preferably be present in the pharmaceutical preparations listed above in a concentration of approx. 0.1 to 99.5 wt. %, preferably from approx. 0.5 to 95 wt. %, of the complete mixture.

Apart from the compounds of the formulae (I) and (III), the pharmaceutical preparations may also contain further pharmaceutical active substances.

The compounds may be used together with hitherto described substances having antibacterial, antiviral, antimycotic and antiparasitic properties. Such substances in particular include compounds which have already been used in therapeutic applications or are still used. Substances which are suitable for this purpose are in particular those listed in the Red List or in Simon/Stille, Antibiokia-Therapie in Klinik und Praxis, 9th edition, 1998, Schatauer Verlag, or on the Internet at http://www.customs.treas.gov/impexp/rulings/harmoniz/hrm129.html. The derivatives may in particular be present with penicillins, benzylpenicillin (penicillin G), phenoxypenicillins, isoxazolylpenicillins, aminopenicillins, ampicillin, amoxicillin, bacampicillin, carboxypenicillin, ticarcillin, temocillin, acylaminopenicillins, azlocillin, mezlocillin, piperacillin, apalcillin, mecillinam, cephalosporins, cefazolin group, cefuroxime group, cefoxitin group, cefoxitin, cefotetan, cefmetazole, latamoxef, flomoxef, cefotaxime group, cefozidime, ceftazidime group, ceftazidime, cefpirome, cefepime, conventional cephalosporins, cefsulodin, cefoperazone, oral cephalosporins of the cephalexin group, loracarbef, cefprozil, new broad-spectrum oral cephalosporins, cefixime, cefpodoxime-proxetil, cefuroxime-axetil, cefetamet, cefotiam-hexetil, cefdinir, ceftibuten, other β-lactam antibiotics, carbapenem, imipenem/cilastatin, meropenem, biapenem, aztreonam, β-lactamase inhibitors, clavulanic acid/amoxicillin, clavulanic acid/ticarcillin, sulbactam/ampicillin, tazobactam/piperacillin, tetracyclines, oxytetracycline, rolitetracycline, doxycycline, minocycline, chloramphenicol, aminoglycosides, gentamicin, tobranycin, netilmicin, amikacin, spectinomycin, macrolides, erythromycin, clarithromycin, roxithromycin, azithromycin, dirithromycin, spiramycin, josamycin, lincosamides, clindamycin, fusidic acid, glycopeptide antibiotics, vancomycin, teicoplanin, pristinamycin derivatives, fosfomycin, antimicrobial folic acid antagonists, sulfonamides, co-trimoxazole, trimethoprim, other diaminopyrimidine-sulfonamnide combinations, nitrofurans, nitrofurantoin, nitrofurazone, gyrase inhibitors (quinolones), norfloxacin, ciprofloxacin, ofloxacin, sparfloxacin, enoxacin, fleroxacin, pefloxacin, lomefloxacin, Bay Y3 118, nitroimidazoles, antimycobacterial agents, isoniazid, rifampicin, rifabutin, ethambutol, pyrazinamide, streptomycin, capreomycin, prothionamide, terizidone, dapsone, clofazimine, topical antibiotics, bacitracin, tyrothricin, polymyxins, neomycin, kanamycin, paromomycin, mupirocin, antiviral agents, acyclovir, ganciclovir, azidothymidine, didanosine, zalcitabine, thiacytidine, stavudine, ribavirin, idoxuridine, trifluridine, foscarnet, amantadine, interferons, tibol derivatives, proteinase inhibitors, antimycotics, polyenes, amphotericin B, nystatin, natamycin, azoles, azoles for septic therapy, miconazole, ketoconazole, itraconazole, fluconazole, UK-109,496, azoles for topical use, clotrimazole, econazole, isoconazole, oxiconazole, bifonazole, flucytosine, griseofulvin, ciclopirox olamine, tolnafnate, naftifine, terbinafine, amorolfine, anthraquinones, betulinic acid, semianthraquinones, xanthones, naphthoquinones, arylamino alcohols, quinine, quinidines, mefloquine, halofantrine, chloroquine, amodiaquine, acridine, benzonaphthyridine, mepacrine, pyronaridine, dapsone, sulfonamides, sulfadoxine, sulfalenes, trimethoprim, proguanil, chlorproguanil, diaminopyrimidines, pyrimethamine, primaquine, aminoquinolines, WR 238,605, tetracycline, doxycycline, clindamycin, norfloxacin, ciprofloxacin, ofloxacin, artemisinin, dihydroartemisinin, 10b artemether, arteether, atresunate, atovaquone, suramin, melarsoprol, nifurtimox, stibogluconate sodium, pentamidine, amphotericin B, metronidazole, clioquinol, mebendazole, niclosamide, praziquantel, pyrantel, tiabendazole, diethylcarbamazine, ivermectin, bithionol, oxamniquine, metrifonate, piperazine, embonate.

The organophosphorus compounds may furthermore be present in the pharmaceutical preparations in combination with sulfonamide, sulfadoxine, artemisinin, atovaquone, quinine, chloroquine, hydroxychloroquine, mefloquine, halofantrine, pyrimethamine, armesin, tetracyclines, doxycycline, proguanil, metronidazole, praziquantel, niclosamide, mebendazole, pyrantel, tiabendazole, diethylcarbazine, piperazine, pyrivinium, metrifonate, oxamrniquine, bithionol or suramin or two or more of these substances.

The above-stated pharmaceutical preparations are produced in the conventional manner using known methods, for example by mixing the active substance or substances with the excipient or excipients.

The stated preparations may be administered to humans and animals orally, rectally, parenterally (intravenously, intramuscularly, subcutaneously), intracisternally, intravaginally, intraperitoneally, topically (powders, ointments, drops) and for the treatment of infections in cavities, body cavities. Suitable preparations which may be considered are solutions for injections, solutions and suspensions for oral therapy, gels, infusion formulations, emulsions, ointments or drops. Topical treatment may be performed using ophthalmological and dermatological formulations, silver and other salts, ear drops, eye ointments, powders or solutions. Administration to animals may also be achieved via the feed or drinking water in suitable formulations. Gels, pulverulent formulations, powders, tablets, controlled-release tablets, premixes, concentrates, granules, pellets, tablets, boli, capsules, aerosols, sprays, inhalation formulations may also be used in humans and animals. The compounds according to the invention may also be incorporated into other supports, such as for example plastics (plastic chains for topical treatment), collagen or bone cement.

It has in general proved advantageous in both human and veterinary medicine to administer the active substances of the formula (I) and (III) in total quantities of approx. 0.05 to approx. 600, preferably of 0.5 to 200 mg/kg body weight per 24 hours, optionally in the form of two or more individual doses in order to achieve the desired results. An individual dose preferably contains the active substance or substances in quantities of approx. 1 to approx. 200, in particular of 1 to 60 mg/kg body weight. It may, however, be necessary to deviate from the stated dosages, in particular as a function of the nature and body weight of the patient to be treated, the nature and severity of the disease, the nature of the preparations and the route of administration of the pharmaceutical preparation and the period of time over which administration is performed.

In some cases, it may accordingly be sufficient to use less than the above-stated quantity of active substance, while in other cases more than the above-stated quantity of active substance must be used. The person skilled in the art will use his/her skill to determine the optimum dosage and route of administration required in each particular case.

The compounds according to the invention may be given to animals in conventional concentrations and preparations together with feed or feed preparations or with drinking water.

The compounds according to the invention are furthermore ideally usable as bactericides, fungicides and herbicides in plants.

The person skilled in the art knows in principle how the substances according to the invention are to be synthesised. Some examples of syntheses are stated below.

EXAMPLES

Synthetic Pathways for Compounds of the Appearance

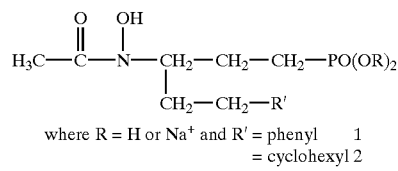

where R = H or $Na^+$ and R' = phenyl  1
= cyclohexyl 2

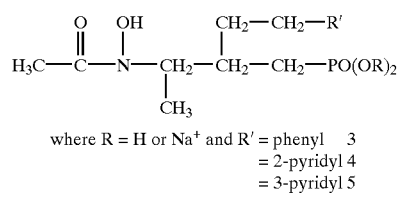

where R = H or $Na^+$ and R' = phenyl  3
= 2-pyridyl 4
= 3-pyridyl 5

Example 1
3-Oxosbutylphosphonic acid diethyl ester (1a)

According to reference R. G. Harvey, Tetrahedron, 1966, 22, 2561–73, 0.1 mol of vinyl methyl ketone and 0.125 mol of triethyl phosphite are initially introduced into 30 ml of phenol and are heated under argon to 100° C. for 24 h. The reaction solution is evaporated up to a temperature of 110° C./8·10$^2$ Pa (6 Torr), with the impure product 1a passing over in the distillate. Purification is performed chromatographically on silica gel with ether/pentane in a 1:1 ratio as mobile solvent.

3-Oxo-5-phenylpentylphosphonic acid diethyl ester (1b)

250 ml of THF are added to a stirred suspension of 300 mmol of sodium hydride, which has been washed with n-pentane, and 280 mmol of 3-oxobutylphosphonic acid diethyl ester (1a) are added dropwise at room temperature. After 2 hours' stirring at constant temperature, the reaction mixture is cooled with an ice/common salt mixture and 1.3 equivalents of n-BuLi are added dropwise. After a further 2 hours' stirring at 0° C., 310 mmol of benzyl bromide (dissolved in 50 ml of THF) are slowly added. The mixture is allowed to rise to room temperature, stirred for a further 3 hours and combined with 20 ml of 1 molar HCl. The reaction solution is poured into iced water, extracted three times with 100 ml portions of chloroform and the combined organic phases are washed with saturated common salt solution. Purification of 1b performed chromatographically on silica gel with methylene chloride and ethyl acetate as mobile solvent. (Reaction conditions, c.f.: B. Resul, J. Stjernschantz, K. No, C. Liljebris, G. Selén, M. Astin, M. Karlsson, L. Z. Bito J. Med. Chem. 1993, 36, 243–248)

(1-Phosphonic acid diethyl ester)-5-phenylpentan-3-one oxime (1c)

1.9 equivalents of hydroxylamine hydrochloride are added to a solution of 18 mmol of 1b in 150 ml of ethanol and the mixture stirred for 24 hours. The mixture is then quenched with 100 ml of water and ethanol and some of the water are removed under reduced pressure until the oxime (1c) precipitates. The product (1c) may be purified by recrystallisation from ether. (Reaction conditions, c.f.: T. M. Baltazor J. Org. Chem. 1980, 45, 2519–22 or O. Tsuge et al. Bull. Chem. Soc. Jpn. 1987, 60, 2463–73)

3-N-(Hydroxylamino)-3-(2-phenylethyl)-propylphosphonic acid diethyl ester (1d)

Sodium cyanoborohydride (NaBH$_3$CN) is used without further purification. 4 mmol of oxime 1c, dissolved in a little methanol, are combined with 2 drops of bromocresol green and 6 n KOH is added dropwise until a colour change from yellow to green is observed. 3 mmol of NaBH$_3$CN are added dropwise, the mixture stirred for 3 hours at room temperature and quenched dropwise with methanol/HCl until a colour change from green to yellow is observed. 10 ml of water are added to the reaction mixture and the pH adjusted to >10 with 6 n KOH. Once the aqueous phase has been saturated with common salt, extraction is performed 5 times with 10 ml portions of chloroform, these combined organic phases are dried over MgSO$_4$ and the solvent is removed under reduced pressure. Purification of hydroxylamine (1d) is performed chromatographically on silica gel. (Reaction conditions, c.f.: R. F. Borch, M. D. Bernstein, D. H. Dupont J. Am. Chem. Soc. 1971, 93, 2897–2904 or A. O. Stewart et al. J. Med. Chem. 1997, 40, 1955–68)

3-(N-Hydroxylamino)-5-phenyl-pentylphosphonic acid (1e)

While the mixture is cooled with ice, 130 ml of conc. HCl are added to 0.06 mol of ester (1d) and the mixture is refluxed for 6 hours (oil bath: 150° C.). Once cool, the yellow/brown colour solution is evaporated under reduced pressure, resuspended in approx. 30 ml of water and treated with activated carbon until a virtually colourless solution is obtained. This solution is again evaporated under reduced pressure, resuspended with approx. 30 ml of water and a pH value of 4–5 is established with NaHCO$_3$. The precipitated white to beige precipitate is filtered and may be washed with water/ethanol. In this manner, 3-N-(hydroxylamino)-5-phenyl-pentylphosphonic acid (1e) is obtained in acceptable yields and is further reacted without purification.

3-N-Acetyl-3-N-(hydroxylamino)-5-phenylpentylphosphonic acid (1)

0.013 mol of 3-(N-hydroxylamino)-5-phenylpentylphosphonic acid (1 e) is initially introduced into 20 ml of water and 4.51 (0.044 mol) of acetic anhydride are added dropwise thereto at room temperature. After 1.5 hours' stirring at constant temperature, the pH is adjusted to 2.5 with 2 n NaOH, the solution is evaporated under reduced pressure, resuspended in 40 ml of water and re-evaporated. This procedure is repeated once. The mixture is then washed repeatedly with ether, the latter being removed by decanting, dissolved in 5–10 ml of ethanol and the rewashed with ether. The aqueous phase is made up to 50 ml and adjusted to a pH value of 6.5 with 2 n NaOH. Once volatile constituents have been stripped out under reduced pressure, the remaining water is removed by combining the mixture with n-butanol, which is likewise removed under reduced pressure (down to an oil pump vacuum). The remaining oil is brought to a boil with isopropanol, which is discarded and the residual glassy resin is ground to a solid which may be recrystallised from methanol by addition of relatively large quantities of acetone.

Example 2
3-N-Acetyl-3-N-(hydroxylamino)-5-cyclohexyl-pentylphosphonic acid (2)

Synthesis of 2 proceeds as described in 1. The only difference is in the second reaction step, in which bromomethylcyclohexane is used instead of benzyl bromide. 3-Oxo-5-cyclohexylpentylphosphonic acid diethyl ester (2b) is consequently obtained instead of 3-oxo-5-phenylpentylphosphonic acid diethyl ester (1b) and is further treated as described above.

Examples 3 to 5

Possible starting materials are the pentan-2-ones substituted on C5 phenyl, 2-pyridyl or 3-pyridyl which have been described in the literature:

5-Phenyl-2-pentanone (3a)

According to reference F. C. Montgomery, W. H. Saunders, Jr. J. Org. Chem. 1976, 41, 2368–72, 7.6 g of sodium are added to 200 ml of absolute ethanol. Once the sodium has dissolved, 43 g (0.33 mol) of ethyl acetoacetate are added dropwise within an hour, the mixture refluxed for 1 hour, 65 g of 2-phenylethyl bromide are slowly added dropwise and the mixture is refluxed again (21 hours). After cooling and filtration, the mixture is distilled. The product is first heated for 5 h to 90° C. with 350 ml of 5% sodium hydroxide, then stirred for 5 hours at the same temperature with 150 ml of 50% sulfuric acid. After cooling, the product is left to stand for 48 hours, extracted with diethyl ether, the combined extracts are dried over sodium sulfate and 3a is finally obtained in good yield by distillation (b.p.: 132–134° C., 2.3 10$^3$ Pa (17 Torr)).

5-(2-Pyridyl)-2-pentanone (4a)

According to reference F. Noel, Albertson J. Am. Chem. Soc. 1950, 72, 2594–99, a reaction mixture comprising 50 g of acetyl acetone, 1.5 g of sodium and 108 g of 2-vinylpyridine is refluxed for 7 hours. The produced may be distilled as a yellow oil at 1.5. 102 Pa (1.1 Torr) (b.p.: 90–127° C.). Fractional distillation of this oil yields 11.9 g of 5-(2-pyridyl)-2-pentanone (4a) with a boiling point of 88–105° C. and 1.3·10$^2$ Pa (1.0 Torr).

5-(3-Pyridyl)-2-pentanone (5a):

(according to J. W. Tilley, P. Levitan, J. Lind, A. F. Welton, H. J. Crowley, L. D. Tobias, M. O'Donnell J. Med. Chem. 1987, 30, 185–93; Swern oxidation of the alcohol) 59.5 ml of oxalyl chloride in 1.4 l of absolute dichloromethane are cooled to −60° C. and 96 ml of absolute DMSO (dissolved in 280 ml of absolute dichloromethane) are slowly added dropwise. After 15 minutes' stirring at −60° C., 93 g of 5-(3-pyridyl)-2-pentanol in 470 ml of the same solvent are added dropwise at −60° C. After 20 minutes' stirring, 396 ml of triethylamine are slowly added, the mixture stirred for a further 20 minutes at −60° C. and allowed to rise to room temperature. The reaction solution is finally poured into 700 ml of iced water, which has previously been combined with NaOH pellets. Once the phases have separated, the aqueous, alkaline phase is extracted 3 times with 300 ml portions of dichloromethane, the combined organic phases are washed 4 times with 500 ml portions of water, dried over potassium carbonate and evaporated. After distillation, 5a of b.p. 98–104° C., 3·10$^1$ Pa (0.2 Torr) is obtained in good yield.

Bromomethylphosphonic acid diethyl ester (3b)

(according to P. C. Crofts, G. M. Kosolapoff J. Am. Chem. Soc. 1953, 75, 5738–40) 126 g of triethyl phosphite and 162 g of dibromomethane are heated to 170° C. in an autoclave for 4 hours. Bromomethylphosphonic acid diethyl ester may be isolated in moderate yield from the reaction mixture by distillation (b.p.: approx. 50° C., 7 Pa (0.05 Torr)). A second fractional distillation was then performed.

Examples 7 to 9

The 3-oxo-2-(2-R'-ethyl)butylphosphonic acid diethyl esters where R'=phenyl, 2-pyridyl and 3-pyridyl are prepared by producing the thermodynamically stabilised trimethylsilylenol ether of the ketones 3a, 4a and 5a and subsequently performing a reaction with bromomethylphosphonic acid diethyl ester (3b):

3-Oxo-2-(2-phenylethyl)butylphosphonic acid diethyl ester (3c)

(Sample reaction of 3a with bromomethylphosphonic acid diethyl ester. This reaction, which proceeds via the thermodynamically stabilised trimethylsilylenol ether, may be performed in the same manner with 4a and 5a.)

Preparation of the trimethylsilylenol ethers: in this case, by way of example: 5-phenyl-2-trimethylsilyl-2-pentanol (3c')

0.25 mol of 5-phenyl-2-pentanone (3a) is added dropwise to 0.3 mol of trimethylchlorosilane and 0.6 mol of triethylamine in 100 ml of absolute dimethylformamide (DMF) and the mixture stirred for 3 days at a temperature of 110° C. Once the solution has been diluted with 200 ml of pentane, it is washed 3 times with 300 ml portions of a cold aqueous solution containing NaHCO$_3$. The organic phase is then washed in succession with cold 1.5 molar aqueous HCl and with cold aqueous NaHCO$_3$ solution, it being necessary to work rapidly at this point. After drying and evaporation under reduced pressure up to the maximum oil pump vacuum, secondary products and starting materials may be removed. The thermodynamically stabilised enol ether 3c' is isolated by high pressure liquid chromatography on a diol phase (UV detection, mobile solvent: dichloromethane, tert.-butyl methyl ether). (Reaction conditions, c.f.: H. O. House, L. J. Czuba, M. Gall, H. D. Olmstead J. Org. Chem. 1969, 34, 2324 and I. Peterson Tetrahedron 1988, 44, 4207–19 and I. Fleming, I. Paterson Synthesis, 1979, 736–38.)

Preparation of the 2-(2-R'-ethyl)-substituted 3-oxobutylphosphonic acid esters: in this case, by way of example: 3-oxo-2-(2-phenylethylbutylphosphonic acid diethyl ester (3c)

5.5 mmol of TiCl$_4$ in 5 ml of absolute dichloromethane are added dropwise at −20° C. under argon to a solution of 5 mmol of O-silylated enolate 3c' and 6 mmol of bromomethylphosphonic acid diethyl ester (3b) in 5 ml of absolute dichloromethane. After approx. 1 hour, the reaction solution is poured into 25 ml of aqueous saturated NaHCO$_3$ solution, the mixture extracted repeatedly with ether, the combined organic phases are dried over MgSO$_4$, evaporated under reduced pressure and the product 3c is purified by column chromatography on silica gel.

3-Oxo-2-(2-phenylethyl)butylphosphonic acid diethyl ester (3c) and 3-oxo-2-[2-(2-pyridyl)ethyl]butylphosphonic acid diethyl ester (4c) and 3-oxo-2-[2-(3-pyridyl)ethyl] butylphosphonic acid diethyl ester (5c) may then, as already described in 1, be transformed by conversion into the oxime, reduction to yield the hydroxylamine, subsequent hydrolysis and acetylation to yield the products 3-acetyl-3-(N-hydroxylamino)-3-methyl-2-(2-phenylethyl) propylphosphonic acid (3) 3-acetyl-3-(N-hydroxylamino)-3-methyl-2-[2-(2-pyridyl)ethyl]propylphosphonic acid (4) and 3-acetyl-3-(N-hydroxylamino)-3-methyl-[2-(3-pyridyl) ethyl]propylphosphonic acid (5). The reaction conditions and all the relationships used are the same as those described in Example 1.

Example 10

Antibacterial action of the above-stated compounds 1 to 5

A dilution series comprising the concentrations 500, 100, 50, 10 and 0 $\mu$mol l$^{-1}$ of the individual compounds 1 to 5 in LB medium is introduced into 5 culture microtubes in a volume of 0.5 ml. Each of the microtubes was inoculated with 10 $\mu$l of an overnight culture of *E. coli* K12 and shaken overnight at 37° C. Bacterial growth was assessed on the basis of the turbidity of the medium. The results are shown in Table 1.

Example 11

The antimalarial activity of compounds 1 to 5 was determined using in vitro cultures of the causative organism of malaria, *Plasmodium falciparum*. 200 $\mu$l of an asynchronous *Plasmodium falciparum* culture with a 0.4% blood parasite content and a haematocrit of 2% were loaded into each of the wells of a 96 well microtitre plate. A serial dilution series of the compounds was then prepared in steps of three between concentrations of 100 and 0.14 $\mu$mol l$^{-1}$. The plates are incubated at 37° C., 3% CO$_2$ and 5% O$_2$ over a period of 48 hours. 30 $\mu$l of medium supplemented with 27 $\eta$Ci ml$^{-1}$ of [$^3$H]-hypoxanthine were then added to each well. After 24 hours' incubation, the parasites were harvested by filtration through glass fibre filters and the incorporated radioactivity was measured. Inhibition of parasite growth was measured as the percentage inhibition of tritium incorporation. Inhibition of parasite growth was measured as the percentage inhibition of tritium incorporation relative to a comparison without the substance. The median inhibitory concentration (IC50) of the substance was determined by extrapolating the values. The results are shown in Table 1.

TABLE 1

| Joints | Example 10 IC 50 values, E. coli (nM) | Example 11 IC 50 values, Plasmodium falciparum (nM) |
|---|---|---|
| 1 | 468 | 215 |
| 2 | 324 | 157 |
| 3 | 762 | 405 |
| 4 | 736 | 375 |
| 5 | 318 | 183 |

What is claimed is:

1. Organophosphorus compounds of the general formula (I)

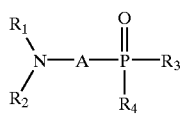

in which $R_1$ and $R_2$ are identical or different and are selected from the group which consists of hydrogen, substituted and unsubstituted $C_{1-9}$ alkyl, substituted and unsubstituted hydroxy-$C_{1-9}$-alkyl, substituted and unsubstituted $C_{1-9}$ alkenyl, substituted and unsubstituted $C_{1-9}$ alkynyl, substituted and unsubstituted aryl, substituted and unsubstituted acyl, substituted and unsubstituted cycloalkyl, substituted and unsubstituted aralkyl, substituted and unsubstituted heterocyclic group, halogen, $OX_1$ and $OX_2$, wherein $X_1$ and $X_2$ may be identical or different and are selected from the group which consists of hydrogen, substituted and unsubstituted $C_{1-9}$ alkyl, substituted and unsubstituted hydroxy-$C_{1-9}$-alkyl, substituted and unsubstituted $C_{1-9}$ alkenyl, substituted and unsubstituted $C_{1-9}$ alkynyl, substituted and unsubstituted aryl, substitutedand unsubstituted acyl, substituted and unsubstituted cycloalkyl, substituted and unsubstituted aralkyl, substituted and unsubstituted heterocyclic group, in which A is of the following formula (II):

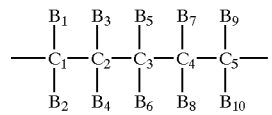

wherein one or more of the carbon atoms selected from the group $C_3$, $C_4$, $C_5$ together with their substituents may also be absent, and at least one substituent present in the range from $B_1$ to $B_{10}$ is a $C_{3-8}$-cycoalkyl-($C_{0-9}$)-alkyl group, wherein both the $C_{3-8}$ cycloalkyl group and the $C_{0-9}$ alkyl group may comprise one or more double bonds and one or two carbon atoms of the cycloalkyl group may be replaced by nitrogen, oxygen or sulfur atoms, and wherein both the cycloalkyl group and the alkyl group may be substituted with hydroxy, halogen, amino, oxo groups with branched or unbranched $C_{1-9}$ alkyl groups and $C_{2-9}$ alkenyl groups, wherein the $C_{1-9}$ alkyl groups and $C_{2-9}$ alkenyl groups may be substituted with hydrogen, hydroxy, amino, halogen and oxo groups, and the remaining substituents $B_1$ to $B_{10}$ present are selected from the group which consists of hydrogen, hydroxy, halogen, amino groups, $C_{1-26}$ alkyl groups, $C_{1-26}$ alkoxy groups, $C_{1-26}$-alkoxy-$C_{1-26}$-alkyl groups or both substituents of a C atom together form an oxo group, wherein each $C_{1-26}$ alkyl group and each $C_{1-26}$ alkoxy group may be branched or unbranched and be saturated or unsaturated with one or more double bonds and may be substituted with hydroxy, amino, halogen and oxo groups, in which $R_3$ and $R_4$ are identical or different and are selected from the group which consists of substituted and unsubstituted $C_{1-26}$ alkyl, substituted and unsubstituted hydroxy-$C_{1-26}$-alkyl, substituted and unsubstituted aryl, substitutedand unsubstituted acyl, substituted and unsubstituted cycloalkyl, substituted and unsubstituted aralkyl, substituted and unsubstituted $C_{1-26}$alkenyl, substituted and unsubstituted $C_{1-26}$alkynyl, substituted and unsubstituted cycloalkyl, substituted and unsubstituted heterocyclic group, halogen, $OX_3$ and $OX_4$, wherein $X_3$ and $X_4$ are identical or different and consist of hydrogen, substituted and unsubstituted $C_{1-26}$ alkyl, substituted and unsubstituted hydroxy-$C_{1-26}$-alkyl, substituted and unsubstituted aryl, substituted and unsubstituted aralkyl, substituted and unsubstituted $C_{1-26}$ alkenyl, substituted and unsubstituted $C_{1-26}$ alkynyl, substituted and unsubstituted cycloalkyl, substituted and unsubstituted heterocyclic group, a silyl, a cation of an organic and inorganic base, a metal of main groups I, II or III of the periodic system, ammonium, substituted ammonium and ammonium compounds derived from ethylenediamine or amino acids, and the pharmaceutically acceptable salts, esters thereof and salts of the esters.

2. Compound according to claim 1, wherein the organophosphorus compounds are of the formula (II)

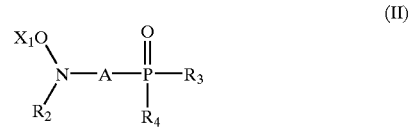

wherein wherein $X_1$ is hydrogen and $R_2$ an acyl group, a formyl group or acetyl group, and $R_3$, $R_4$ and A have the same meaning as in formula (I).

3. Compound according to claim 1, wherein $X_3$ and $X_4$ are selected from the group which consists of $OX_3$ and $OX_4$, and $X_3$ and $X_4$ are selected from the group comprising hydrogen, a metal of main groups I, II or III of the periodic system, ammonium, substituted ammonium, or ammonium compounds derived from ethylenediamine or amino acids.

4. Compound according to claim 1, wherein the carbon chain of A with the formula (II) consists of three carbon atoms $C_1$, $C_2$, $C_3$.

5. Compound according to claim 1, wherein $B_1$ and $B_2$ together or $B_7$ and $B_8$ together form an oxo group and the carbon chain in A consists of four carbon atoms $C_1$, $C_2$, $C_3$, $C_4$.

6. Compound according to claim 1, wherein the carbon chain of A with the formula (II) consists of four carbon atoms $C_1$, $C_2$, $C_3$, $C_4$ and $B_7$ or $B_8$ or both are a hydroxy group.

7. Compound according to claim 1, wherein the carbon chain consists of 5 carbon atoms $C_1$, $C_2$, $C_3$, $C_4$, $C_5$, wherein $B_1$ and $B_2$ together form an oxo group and $B_9$ or $B_{10}$ are a hydroxyl group or $B_9$ and $B_{10}$ together also form an oxo group.

8. Compound according to claim 6, wherein $R_3$ or $R_4$ or both are methylene groups.

9. A pharmaceutical preparation for the treatment of infectious processes in humans and animals which are caused by viruses, bacteria, fungi or parasites and as a fungicide, bactericide or herbicide in plants, comprising a therapeutically effective amount of an organophosphorous compound according to claim 1, and a pharmaceutically acceptable carrier.

10. A therapeutic method for the treatment of infectious processes in humans and animals which are caused by viruses, bacteria, fungi or parasites and as a fungicide, bactericide or herbicide in plants, comprising administering to a subject selected from the group consisting of a human, an animal, and a plant, a therapeutically effective amount of an organophosphorus compound according to claim 1.

11. A method according to claim 10, wherein the infections are caused by bacteria, viruses, fungi or unicellular parasites or multicellular parasites.

12. A method according to claim 10, wherein the infections are caused by bacteria which are selected from the group which consists of bacteria of the family Propionibacteriaceae, the genus Propionibacterium, the species Propionibacterium acnes, bacteria of the family Actinomycetaceae, the genus Actinomyces, bacteria of the genus Cornynebacterium, the species *Corynebacterium diphtheriae* and *Corynebacterium oseudotuberculosis*, bacteria of the family Mycobacteriaceae, of the genus Mycobacterium, the species *Mycobacterium leprae, Mycobacterium tuberculosis, Mycobacterium bovis* and *Mycobacterium avium*, bacteria of the family Chlamydiaceae, the species *Chlamydia trachomatis* and *Chlamydia psittaci*, bacteria of the genus Listeria, the species Listeria monocytogenes, bacteria of the species *Erysipelthrix rhusiopathiae*, bacteria of the genus Clostridium, bacteria of the genus Yersinia, the species *Yersinia pestis, Yersinia pseudotuburculosis, Yersinia enterocolitica* and *Yersinia ruckeri*, bacteria of the family Mycoplasmataceae, of the genera Mycoplasma and Ureapiasma, the species Mycoplasma pneumoniae, bacteria of the genus Brucella, bacteria of the genus Bordetella, bacteria of the family Nesseriaceae, of the genera Neisseria and Moraxella, the species *Neisseria meningitides, Neisserla gonorrhoeae* and *Moraxella bovis*, bacteria of the family Vibrionaceae, the genera Vibrio, Aeromonas, Plesiomonas and Photobacterium, the species *Vibrio cholerae, Vibrio anguillarum* and *Aeromonas salmonicidas*, bacteria of the genus Campylobacter, the species *Campylobacter jejuni, Campylobacter coli* and *Campylobacter fetus*, bacteria of the genus Helicobacter, the species *Helicobacter pylori*, bacteria of the families Spirochaetaceae and Leptospiraceae, the genera Treponema, Borrelia and Leptospira, *Borrelia burgdorferi*, bacteria of the genus Actinobacillus, bacteria of the family Legionellaceae, of the genus Legionella, bacteria of the family Rickettsiaceae and family Bartonellaceae, bacteria of the genera Nocardia and Rhodococcus, bacteria of the genus Dermatophilus, bacteria of the family Pseudomonadaceae, the genera Pseudomonas and Xanthomonas, bacteria of the family Enterobacterlaceae, the genera Escherichia, Klebsiella, Proteus, Providencia, Salmonella, Serratia and Shigella, bacteria of the family Pasteurellaceae, the genus Haemophilus, bacteria of the family Micrococcaceae, the aenera Micrococcus and Staphylococcus, bacteria of the family Streptococcaceae, the genera Streptococcus and Enterococcus and bacterial of the family Bacillaceae, the genera Bacillus and Clostridium, and in the eradication of Helicobacter in ulcers of the gastrointestinal tract.

13. A method according to claim 10, wherein the infections are caused by viruses which are selected from the group which consists of viruses of the genus Parvoviridae, parvoviruses, dependoviruses, densoviruses, viruses of the genus Adenoviridae, adenoviruses, mastadenoviruses, aviadenoviruses, viruses of the genus Papovaviridae, papovaviruses, papillomaviruses, polyomaviruses, JC virus, BK virus and miopapovaviruses, viruses of the genus Herpesviridae, herpes simplexviruses, varicella-zoster viruses, human cytomegalovirus, Epstein-Barr viruses, human herpesvirus 6, human herpesvirus 7, human herpesvirus 8, viruses of the genus Poxiviridae, poxviruses, orthopoxviruses, parapoxviruses, molluscum contagiosum virus, aviviruses, capriviruses, leporipcxviruses, primarily hepatotropic viruses, hepatitsviruses, hepatitis A viruses, hepatitis B viruses, hepatitis C viruses, hepatitis D viruses, hepatitis E viruses, hepatitis F viruses, hepatitis G viruses, hepadnaviruses, all hepatitisviruses, hepatitis 3 virus, hepatitis D viruses, viruses of the genus Piccrnaviridae, picornaviruses, all enteroviruses, all polioviruses, all coxsackie-viruses, all echoviruses, all rhinoviruses, hepatitis A virus, aphthoviruses, viruses of the genus Calcivlridae, hepatitis E viruses, viruses of the genus Reoviridae, reoviruses, orbiviruses, rotaviruses, viruses of the genus Togaviridae, togaviruses, alphaviruses, rubiviruses, pestiviruses, rubellavirus, viruses of the genus Flaviviridae, flaviviruses, FSME virus, hepatitis C virus, viruses of the genus Orthomyxoviridae, all influenza viruses, viruses of the genus Paramyxoviridae, paramyxoviruses, morbillivirus, pneumovirus, measles virus, mumps virus, viruses of the genus Rhabdoviridae, rhabdoviruses, rabies virus, lyssavirus, vascular stomatitisvirus, viruses of the genus Coronaviridae, coronaviruses, viruses of the genus Bunyaviridae, bunyaviruses, nairovirus, phlebovirus, uukuvirus, hantavirus, hantaan virus, viruses of the genus Arenaviridae, arenaviruses, lymphocytic choriomeningitis virus, viruses of the genus Retroviridae, retroviruses, all HTL viruses, human T-cell leukaemia virus, oncornaviruses, spumaviruses, lentiviruses, all HI viruses, viruses of the genus Filbviridae, Marburg and Ebola virus, slow-viruses, prions, oncoviruses and leukaemia viruses.

14. A method according to claim 10, wherein the infections are caused by unicellular parasites comprising the causative organisms of malaria, sleeping sickness, Chagas' disease, toxoplasmosis, amoebic dysentery, leishmaniases, trichomoniasis, pneumocystosis, balantidiasis, cryptosporidiosis, sarcocytosis, acanthamoebosis, naeglerosis, coccidiosis, giardiasis and lambliasis.

* * * * *